United States Patent [19]
Gordon

[11] Patent Number: 5,827,305
[45] Date of Patent: Oct. 27, 1998

[54] TISSUE SAMPLING DEVICE

[76] Inventor: Mark G. Gordon, 615 Orchid, Corona Del Mar, Calif. 92625

[21] Appl. No.: 801,814

[22] Filed: Feb. 14, 1997

Related U.S. Application Data

[63] Continuation-in-part of Ser. No. 593,532, Jan. 24, 1996.
[51] Int. Cl.$^6$ ................................................ A61B 17/32
[52] U.S. Cl. ............................................. 606/159; 606/170
[58] Field of Search ................................ 606/1, 170, 174, 606/159, 180; 128/750–755; 604/22

[56] References Cited

U.S. PATENT DOCUMENTS

| | | |
|---|---|---|
| 3,606,878 | 9/1971 | Kellogg, Jr. . |
| 3,818,913 | 6/1974 | Wallach . |
| 3,967,377 | 7/1976 | Wells . |
| 3,994,297 | 11/1976 | Kopf . |
| 4,105,500 | 8/1978 | Libman et al. . |
| 4,263,922 | 4/1981 | White . |
| 4,289,648 | 9/1981 | Hoskins et al. . |
| 4,316,473 | 2/1982 | Beskin . |
| 4,370,987 | 2/1983 | Bazell et al. . |
| 4,385,637 | 5/1983 | Akhavi . |
| 4,457,753 | 7/1984 | Pastrone . |
| 4,517,977 | 5/1985 | Frost . |
| 4,533,348 | 8/1985 | Wolfe et al. . |
| 4,577,629 | 3/1986 | Martinez . |
| 4,662,869 | 5/1987 | Wright . |
| 4,674,502 | 6/1987 | Imonti . |
| 4,696,298 | 9/1987 | Higgins et al. . |
| 4,705,035 | 11/1987 | Givens . |
| 4,706,669 | 11/1987 | Schlegel . |
| 4,750,491 | 6/1988 | Kaufman et al. . |
| 4,796,623 | 1/1989 | Krasner et al. . |
| 4,909,249 | 3/1990 | Akkas et al. . |
| 4,911,161 | 3/1990 | Schechter . |
| 4,986,827 | 1/1991 | Akkas et al. . |
| 4,997,437 | 3/1991 | Grieshaber . |
| 5,011,498 | 4/1991 | Kurmeich et al. . |
| 5,019,035 | 5/1991 | Missirlian et al. . |
| 5,057,098 | 10/1991 | Zelman ..................................... 604/22 |
| 5,074,311 | 12/1991 | Hasson .................................... 128/755 |
| 5,084,059 | 1/1992 | Metzger . |
| 5,234,436 | 8/1993 | Eaton et al. . |
| 5,250,065 | 10/1993 | Clement et al. . |
| 5,261,923 | 11/1993 | Soares . |
| 5,285,795 | 2/1994 | Ryan et al. . |
| 5,318,589 | 6/1994 | Lichtman . |
| 5,385,570 | 1/1995 | Chin et al. . |
| 5,415,182 | 5/1995 | Chin et al. . |
| 5,439,474 | 8/1995 | Li ........................................... 128/754 |
| 5,511,556 | 4/1996 | DeSantis . |
| 5,524,634 | 6/1996 | Turkel et al. . |
| 5,526,822 | 6/1996 | Burbank et al. . |
| 5,562,102 | 10/1996 | Taylor . |
| 5,564,436 | 10/1996 | Hakky et al. . |
| 5,573,008 | 11/1996 | Robinson et al. . |

OTHER PUBLICATIONS

One Page Brochure, "Sever the Ties That Bind", By Visitec.
"Vitreous Microsurgery", Second Edition, By Steve Charles, M.D., (pp. 25–41, 19 pages total), Copyright 1987.

*Primary Examiner*—William Lewis
*Attorney, Agent, or Firm*—Stetina Brunda Garred & Brucker

[57] ABSTRACT

A tissue sampling device for retrieving multiple tissue samples from a body has a catheter and a tissue collector formed proximate the distal end of the catheter. The tissue collector is configured so as to facilitate the removal of a tissue sample from its in-situ anatomical location and so as to capture the tissue sample within the first lumen of the catheter. A passage provides fluid communication between a first lumen within which the collected tissue sample is disposed and a second lumen into which a fluid may be caused to flow. Flowing the fluid distally through the second lumen moves the tissue sample proximally through the first lumen so as to facilitate the collection of a plurality of such tissue samples.

33 Claims, 3 Drawing Sheets

TISSUE SAMPLING DEVICE

Related Applications

This patent application is a continuation-in-part patent application of U.S. Ser. No. 08/593,532, filed Jan. 24, 1996 still pending and entitled ANTERIOR CAPSULOTOMY DEVICE AND PROCEDURE, the contents of which are incorporated by reference.

BACKGROUND OF THE INVENTION

Devices utilized to extract tissue from a patient, typically so as to facilitate the performance of a biopsy thereon, are well known. Such devices are commonly utilized to obtain samples of tissue which is suspected of being cancerous or otherwise diseased. Such tissue samples are typically examined by a doctor or laboratory personnel so as to facilitate a diagnosis.

As those skilled in the art will appreciate, such tissue sampling devices are frequently utilized to sample tissue from the colon and other portions of the gastrointestinal tract, as well as from the liver, lungs, breasts, prostate, and various other anatomical structures of the body. Indeed, many different applications for such tissue sampling devices have been found.

According to the prior art, such contemporary tissue sampling devices generally extract a sample of the desired tissue from the body via a hollow needle, catheter, or the like utilizing an externally applied vacuum. However, as those skilled in the art will appreciate, the use of such an externally applied vacuum suffers from several inherent deficiencies. Among these inherent deficiencies are the requirement for a vacuum system, which entails both the costs associated with initial installation thereof, as well as periodic maintenance thereof.

Further, the use of such externally applied vacuum to facilitate the retrieval of tissue samples from the body complicates the tissue extraction process. As those skilled in the art will appreciate, it is necessary to discontinue the application of the externally applied vacuum so as to facilitate removal of the tissue sample from the sampling device. Thus, the vacuum source must be valved off so as to facilitate access to the tissue sample, which is typically contained within a collection container.

Further, when a common collection container is so utilized to temporarily store such a plurality of tissue samples, the order in which the tissue samples have been taken is not preserved. Thus, when it is necessary to preserve the sequence with which tissue samples are taken, so as to facilitate their association to their in-situ locations, the collection container must be emptied after each sample is taken, thereby further complicating the procedure. It is extremely undesirable to complicate the tissue sampling procedure, since such complications inherently prolong the task, thus increasing discomfort and risk to the patient and also requiring more of the physician's time.

In view of the foregoing, it is beneficial to provide a tissue sampling device which does not require the application of an externally applied vacuum so as to facilitate the extraction of tissue samples, and which preserves the sequence in which the tissue samples are taken so as to facilitate their later association with the specific in-situ location at which each of the tissue samples were collected.

SUMMARY OF THE INVENTION

The present invention specifically addresses and alleviates the above-mentioned deficiencies associated with the prior art. More particularly, the present invention comprises a tissue sampling device for retrieving multiple tissue samples from a body. The tissue sampling device comprises a catheter having a proximal end and a distal end, the catheter comprising first and second lumens; a tissue collector formed proximate the distal end of the catheter for removing a tissue sample from its in-situ anatomical location and for capturing the tissue sample within the first lumen of the catheter; and a passage providing fluid communication between the first and second lumens, the passage being configured such that fluid flowed distally through the second lumen moves the tissue sample proximally through the first lumen. Moving the tissue sample proximally through the first lumen facilitates collection of a plurality of such tissue samples. As discussed in detail below, the plural tissue samples are maintained in the order in which they were collected, such that each of the tissue samples may later be properly associated with the specific in-situ anatomical location from which it was removed. According to the preferred embodiments of the present invention, the first lumen is larger than the second lumen, so as to accommodate the tissue sample.

Preferably, a deflector directs fluid from the second lumen to the first lumen and is preferably configured to so as to direct a substantial portion of the fluid distal of the tissue sample, so as to move the tissue sample proximally. Thus, when it is desired to move the tissue sample so as to facilitate the collection of subsequent tissue sample, the user injects additional fluid, preferably saline solution, into the second lumen, so as to cause the previously collected tissue sample to move proximally. Thus, by alternately collecting tissue samples and injecting water into the first lumen, a plurality of such tissue samples, separated by a quantity of water, become disposed along the length of the first lumen.

According to a first preferred embodiment of the present invention, the deflector comprises a protuberance formed upon an inner will of the catheter for directing the fluid from the second lumen into the first lumen.

According to a second preferred embodiment of the present invention, the deflector comprises an end cap for the catheter. More particularly, according to the second preferred embodiment of the present invention, the deflector comprises a channel formed in the end cap for directing the fluid from the second lumen into the first lumen.

The tissue collector preferably comprises a seal for mitigating fluid leaking from within the collector. The seal assures proper closure of the opening through which the tissue sample is collected and preferably comprises a hermetic seal. Thus, the seal prevents leakage of the fluid injected into the first lumen so as to effect proximal movement of the collected tissue sample. Otherwise, a substantial quantity of such fluid may leak from the catheter, potentially having undesirable effects upon the patient and inhibiting desirable movement of the tissue sample proximally through the first lumen.

The tissue collector is preferably configured to cut tissue away from its in-situ anatomical location. Alternatively, the tissue collector is configured so as to cut and/or tear tissue away from its in-situ anatomical location.

According to the preferred embodiment of the present invention, a check valve is disposed proximate the proximal end of the catheter and in fluid communication with the first lumen so as to facilitate fluid flow proximally therethrough while mitigating fluid flow distally therethrough. Thus, the check valve allows fluid to flow distally through the second lumen of the catheter and to flow proximally through the first lumen thereof.

A valved port in full communication with the first lumen facilitates the withdrawal of tissue samples. To withdraw a tissue sample, the valved port is opened, i.e., a valve is turned to the open position and/or a stopper is removed from the port. A small quantity of fluid is then caused to flow distally through the second lumen, so as to urge the tissue sample proximally along the first lumen, and through the valved port. As used herein, the term valved port shall be defined as a port which may be opened and closed, as desired, and shall include a port having a valve formed thereon, as well as a stoppered port.

The fluid preferably comprises a saline solution, or any biocompatible solution and is preferably caused to flow distally within the second lumen via a syringe or squeeze bulb attached to the proximal end of the second lumen. As those skilled in the art will appreciate, various other means, e.g., a pump, a gravity feed container, a gas pressurized ullage, etc., may alternatively be utilized to effect such fluid flow.

According to the preferred embodiment of the present invention, the catheter is configured so as to pass through the working channel of an endoscope or similar medical device, so as to facilitate the desired placement of the distal end of the tissue sampling device, and thereby facilitate the collection of tissue samples from the desired location. Thus, the first and second embodiments of the present invention are preferably configured so as to have a diameter of approximately 2.8 mm or less. As those skilled in the art will appreciate, the use of an endoscope facilitates imaging of the in-situ location of the tissue sample prior to and during the collection process, so as to assure that the tissue sample is taken from the desired location. The distal end of the tissue sampling device of the present invention may further comprise a radiographic marker, such as a radiopaque or radiodense material, so as to facilitate radiological imaging thereof.

Further, those skilled in the art will appreciate that various different guide catheters, trocars, cannulae, etc., may be utilized to facilitate desired positioning of the tissue sampling device of the present invention.

According to the first embodiment of the present invention, the tissue sampling device comprises a blade formed upon the distal end of the catheter; a cap hingedly attached to the distal end of the catheter, the cap having an open position wherein a tissue sample can be urged into the first lumen of the catheter and having a closed position which substantially seals the catheter; an actuator for moving the cap from the open position to the closed position thereof; and a passage providing fluid communication between the first and second lumens, the passage being configured such that fluid flowed through the second lumen causes the tissue sample to move proximally through the first lumen. Causing the actuator to move the cap from the open position to the closed position thereof facilitates removal of the tissue sample from its in-situ anatomical location and facilitates capturing of the tissue sample within the catheter. Moving the tissue sample proximally through the first lumen facilitates collection of a plurality of such tissue samples while monitoring the collection order thereof.

The blade is preferably formed upon a beveled tip of the catheter so as to better facilitate engagement with and cutting of the sampled tissue. According to the preferred embodiment of the present invention, the blade comprises a sharpened edge of the distal end of the catheter. That is, the blade is formed by forming the material of the catheter itself so as to have a sharpened edge. Alternatively, a polymeric material having greater rigidity than that of the remainder of the catheter may be formed to the distal end of the catheter, so as to better facilitate the formation of a sharpened edge thereupon. As a further alternative, a metal blade may be attached to the distal end of the catheter.

The cap is preferably attached to the catheter via a living hinge. The cap is preferably configured so as to be biased in the open position thereof. Thus, the cap moves to the open position thereof when not actuated. According to the preferred embodiment of the present invention, the cap is formed from a portion of the catheter wall itself, and is thus curved in a manner which biases the cap in the open position. That is, since the cap is curved in the same manner in which the catheter wall is curved, the living hinge (also formed from the catheter wall) tends to maintain the cap in the open position thereof. optionally, a spring may be utilized to maintain the cap in the open position thereof.

The actuator preferably comprises a cam formed upon the cap and a sheath, i.e., another catheter, within which the catheter is disposed, such that moving of the sheath distally with respect to the catheter causes the distal end of the sheath to engage the cam, and thus urging the cap into the closed position thereof. Conversely, moving the sheath proximal with respect to the catheter causes the distal end of the sheath to disengage the cam, thus permitting the cap to move back to the open position thereof. Such movement of the cap from the closed position to the open position thereof is partially due to the inherent spring or resilient nature of the living hinge and partially due to the curved or bowed configuration thereof which tends to cause the cap to assume the position of the portion of the catheter wall from which it was originally formed.

According to the second embodiment of the present invention, the tissue sampling device comprises a catheter having a proximal end, a distal end, and a lumen; a sheath having a proximal end, a distal end, and a lumen, the catheter being slidably disposed within the lumen of the sheath; a cap closing the distal end of the inner catheter; an opening formed in the catheter proximate the distal end thereof; and a blade formed at the distal end of the sheath such that sliding the sheath distally with respect to the inner cannula results in cutting of tissue extending from its in-situ anatomical location through the opening formed in the catheter. A passage provides fluid communication between the first and second lumens. The passage is configured such that fluid flowed through the lumen causes the tissue sample to move proximally through the lumen. Again, moving the tissue sample proximally through the first lumen facilitates collection of a plurality of such samples.

The inner cannula preferably fits within the outer cannula or sheath with a clearance of between approximately b 0.001inch and approximately 0.003 inch.

The cap further comprises a deflector for directing fluid from the second lumen into the first lumen. The deflector preferably comprises a channel formed in the cap.

The blade preferably comprises a sharpened portion of the distal end of the sheath, preferably a metal blade attached to the distal end of the sheath. Alternatively, the distal end of the sheath itself may be sharpened, and may alternatively comprise a polymer which is more rigid than the remainder of the catheter.

Thus, according to the methodology for collecting multiple tissue samples of the present invention, the distal end of the catheter is positioned proximate the tissue to be sampled. The tissue sample is then removed from its in-situ anatomical location and captured within the catheter. The fluid is then flowed through the catheter so as to cause the tissue sample to move proximally. As mentioned above, moving the tissue sample proximally through the catheter facilitates collection of a plurality of such tissue samples.

As those skilled in the art will appreciate, collecting multiple tissue samples according to the methodology of the present invention results in the tissue samples being disposed in a spaced apart configuration within the catheter such that the sequence of their collection is preserved. Thus, the first tissue sample collected will be the most proximal tissue sample disposed within the catheter and will be the first tissue sample removed from the proximal end of the catheter.

Maintaining the collected sequence of the tissue sample facilitates the collection of a plurality thereof in a manner which allows each tissue sample to be associated with its in-situ anatomical location. Thus, a plurality of such tissue samples may be taken from a corresponding plurality of different anatomical locations and each tissue sample later associated with its proper collection site.

During the collection process, as each tissue sample is captured within the first lumen of the catheter, the opening in the catheter through which the tissue sample was collected is closed and fluid is caused to flow through the second lumen of the catheter, so as to urge that tissue sample, as well as any previously collected tissue samples, proximally. This is preferably accomplished by filling either a syringe or a squeeze ball or bulb with saline solution and injecting the saline solution into the proximal end of the second lumen. This causes the saline solution to flow through the second lumen of the catheter and to enter the first lumen thereof at a point just distal of the most-recently collected tissue sample, so as to urge that tissue sample as well as all other tissue samples proximally.

Preferably, the tissue collector is configured so as to cut each tissue sample from its in-situ anatomical location. Alternatively, the tissue collector may be configured so as to tear the tissue sample from its in-situ anatomical location. The tissue collector may perform a combination of such cutting and tearing, so as to facilitate the removal of a tissue sample from its in-situ anatomical location.

These, as well as other, advantages of the present invention will be more apparent from the following description and drawings. It is understood that changes in the specific structure shown and described may be made within the scope of the claims without departing from the spirit of the invention.

DETAILED DESCRIPTION OF THE PREFERRED EMBODIMENT

The detailed description set forth below in connection with the appended drawings is intended as a description of the presently preferred embodiments of the invention, and is not intended to represent the only forms in which the present invention may be constructed or utilized. The description sets forth the functions and sequence of steps for constructing and operating the invention in connection with the illustrated embodiments. It is to be understood, however, that the same or equivalent functions may be accomplished by different embodiments that are also intended to be encompassed within the spirit and scope of the invention.

The tissue sampling device of the present invention is illustrated in FIGS. 1–11 which depict two presently preferred embodiments thereof. Referring now to FIGS. 13, the first embodiment of the present invention generally comprises a catheter 10 having a blade 12 formed upon the distal end 14 thereof. A cap 16 is formed at the distal end 14 of the catheter 10 and has an open position wherein a tissue sample may be urged into the catheter 10 and a closed position wherein the tissue sample is captured within catheter 10. The cap 16 is preferably attached to the distal end 14 of the catheter 10 via a living hinge 18 and is preferably formed from the wall of the catheter 10 itself. The cap 16 is preferably slightly bent or bowed (as is the wall of the catheter 10), so as to be biased in the open position thereof. If the cap 16 is formed of the wall of the catheter 10, then the pre-existing curvature thereof may suffice to provide such a bend or bow so as to effect such biasing thereof. Optionally, a spring, such as a metal or polymer spring, may be attached to the cap 16 and the catheter 10, so as to bias the cap 16 in the open position thereof. Those skilled in the art will appreciate that various different configurations of springs and means for attaching the springs are suitable.

Figure 1:
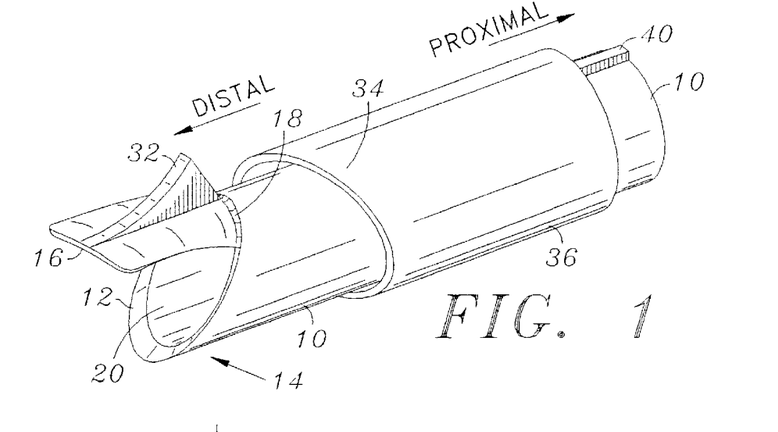
FIG. 1 is a perspective view of the distal portion of a first embodiment of the tissue sampling device of the present invention wherein a cap hingedly attached to the distal end of the catheter closes so as to cut the desired tissue sample away from its in-situ anatomical location and so as to capture the tissue sample within the catheter.
Figure 2:
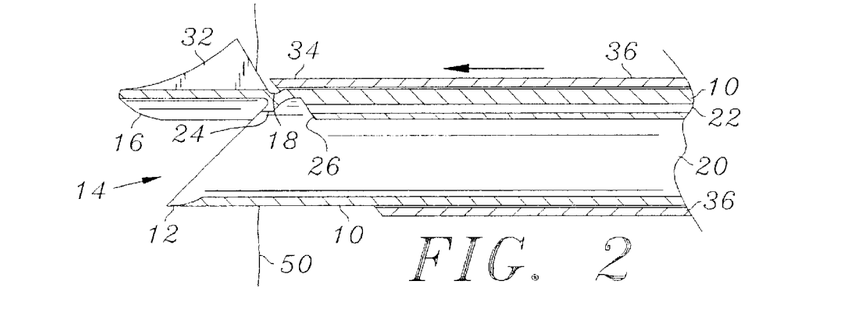
FIG. 2 is a cross-sectional side view of the distal portion of a tissue sampling device of FIG. 1, showing the cap in the open position thereof.
Figure 3:
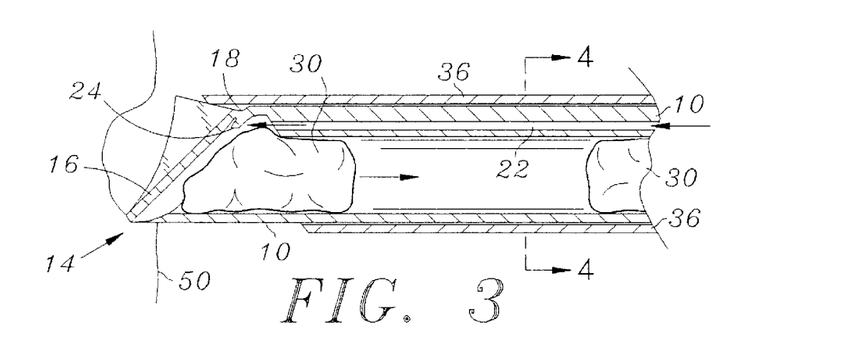
FIG. 3 is a cross-sectional side view of the distal portion of a tissue sampling device of FIG. 1, showing the cap in the closed position thereof, and also showing how fluid flow from the second lumen to the first lumen of the catheter urges tissue samples proximally.

The cap 16 preferably comprises a tapered surface 17 which assures a tight fit within the end of the catheter 10, so as to assure adequate sealing thereof.

The catheter 10 comprises a first lumen 20 within which the tissue sample is captured (as shown in FIG. 3) and a second lumen 22 through which fluid may be caused to flow distally so as to urge a captured tissue sample proximally. A deflector 24 is preferably formed proximate the exit port 26 of the second lumen 22 so as to direct fluid flowing from the second lumen 22 in a manner which effects movement of the tissue sample proximally.

An actuator moves the cap 16 from the open position to the closed position thereof, so as to effect removal of the desired tissue samples from its in-situ anatomical location and so as to effect capture of that sample within the first lumen 20 of the catheter 10. The actuator preferably comprises a cam 32 formed upon the cap 16 so as to be engaged by the distal end 34 of a sheath 36 when the sheath 36 is moved distally with respect to the catheter 10. Thus, as the sheath 36 is moved distally, the distal end 34 thereof contacts the cam 32 and urges the cap 16 into the closed position thereof, wherein the cap 16 closes and seals the catheter 10, so as to capture the collected tissue sample 30 therein and so as to prevent fluid leakage therefrom. The sheath 36 is preferably formed so as to have a bevel formed at the distal end 34 thereof. The bevel formed at the distal end 34 of the sheath 36 is preferably oriented opposite that of the bevel of the catheter 10, i.e., the point of the bevel of the catheter 10 being diametrically opposed to the point of the bevel of the sheath 36. Such configuration of the bevels of the catheter 10 and the sheath 36 tend to prevent interference with the cutting process, such as might occur as the sheath 36 is urged distally.

Figure 4:
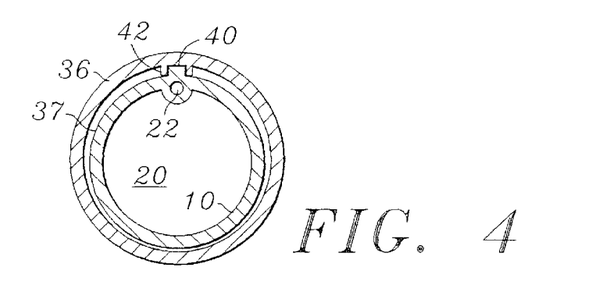
FIG. 4 is a cross-sectional end view taken along lines 4 of FIG. 3, showing the first and second lumens of the catheter and also showing one way in which the catheter may be keyed to the sheath so as to prevent the relative rotations thereof.

Referring now to FIG. 4, in order to maintain the desired orientation of the sheath 36 with respect to the catheter 10, a key 40 is preferably formed upon the catheter 10 and is received within a keyway 42 formed within the sheath 36. The key 40 and the keyway 42 preferably extend along a substantial length of the catheter 10 and the sheath 36, respectively. Those skilled in the art will appreciate the various other means for maintaining the desired orientation of the catheter 10 with respect to the sheath 36 are likewise suitable. For example, both the catheter 10 and the sheath 36 may alternatively be generally in oval in shape, so as to prevent relative rotation of the sheath 36 with respect to the catheter 10.

The clearance 37 between the catheter 10 and the sheath 36 is preferably between approximately 0.001 inch and approximately 0.003 inch.

In use, the first embodiment of the tissue sampling device of the present invention is guided to a desired anatomical location, typically via an endoscope or like device. At the in-situ anatomical location of the desired tissue sample, the distal end 14 of the tissue sampling device is pushed into the tissue 50 to be sampled, thereby forcing a portion 30 of the tissue into the first lumen 20. The first embodiment of the tissue sampling device of the present invention is configured so as to facilitate either straight on sampling or side sampling. Straight on sampling occurs when the catheter is oriented generally perpendicular to the surface of the tissue to be sampled and side sampling occurs when the catheter is oriented generally parallel to the surface of the tissue to be sampled.

Then, the sheath 36 is pushed distally while holding the catheter 10 in place, so as to cause the distal end 34 of the sheath 36 to cam the cap 16 closed, thereby removing, cutting and/or tearing, the tissue sample 30 from its in-situ anatomical location and capturing the tissue sample 30 within the first lumen 20 of the catheter 10. This process may be repeated, as desired, so as to effect the collection of a plurality of such tissue samples 30 within the first lumen 20 of the catheter 10.

Figure 8:
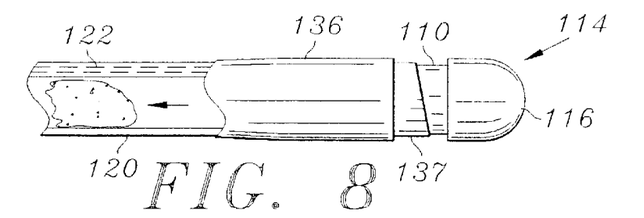
FIG. 8 is an enlarged side view of the distal end of the tissue sampling device of FIG. 7, partially in section, showing fluid urging a tissue sample proximally.
Figure 9:
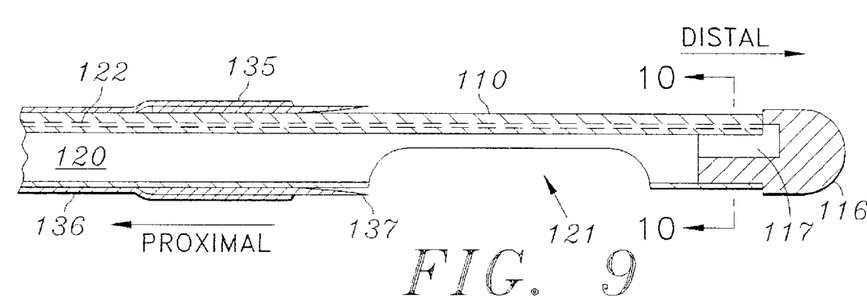
FIG. 9 is an enlarged cross-sectional side view of the distal end of the tissue sampling device of FIG. 8, showing the blade and fluid deflector thereof.
Figures 10, 11:
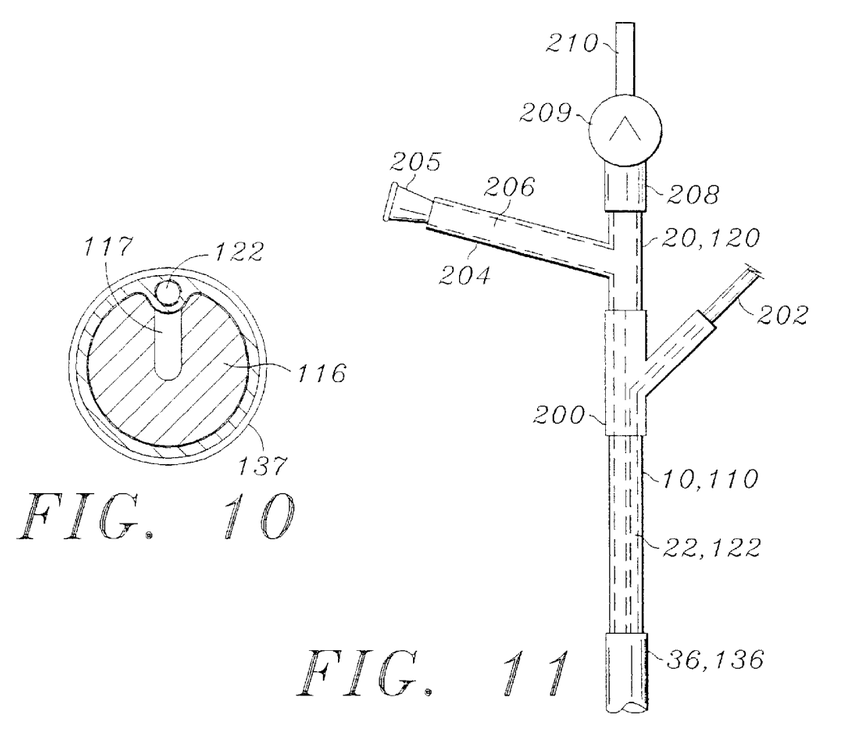
FIG. 10 is a cross-sectional end view of the cap and catheter of FIG. 9, taken along line 10 thereof.
FIG. 11 is a side view of the proximal end of the catheter of the first or second embodiment of the tissue sampling device of the present invention, showing the check valve and the valved port in fluid communication with the first lumen thereof, and also showing a fluid source port in fluid communication with the second lumen.

Referring now to FIGS. 8–10, a second embodiment of the tissue sampling device of the present invention is shown. According to the second embodiment of the present invention, a catheter 110 has a first lumen 120 and a second lumen 122. The distal end 114 of the catheter 110 is closed with a cap 116. An opening 121 is formed in the catheter 110 so as to allow the tissue sample to be urged into the first lumen 120 thereof. The second embodiment of the tissue sampling device of the present invention is configured primarily for side sampling. Thus, the second embodiment of the tissue sampling device is typically utilized when the surface of the tissue to be sampled is oriented generally parallel to the catheter 110. However, as those skilled in the art will appreciate, the second embodiment of the tissue sampling device of the present invention may be manipulated so as to collect tissue samples for various different orientations of the surface of the tissue to be sampled. A sheath 136, within which the catheter 110 is slidably disposed, is configured so as to substantially cover the opening 121 and so as to cut and/or tear a tissue sample away from its in-situ anatomical location when the sheath 136 is moved from its distal position to the proximal position thereof.

The cap 116 preferably comprises a channel 117 formed therein so as to deflect fluid flowing distally within the second lumen into the first lumen 120 such that it urges any tissue samples contained within the first lumen 120 proximally.

The sheath 136 comprises a blade 137 formed at the distal end 135 thereof, so as to effect cutting of the tissue sample away from its in-situ anatomical location after the tissue sample has been urged into the opening 121 of the first lumen 120 discussed in detail below. The blade 137 preferably comprises a metal blade. Alternatively, the blade 137 comprises a sharpened portion of the distal end 135 of the sheath 136. The blade 137 may comprise a polymer having a greater rigidity than that of the sheath 136, which is preferably flexible so as to facilitate its use in tortuous vessels and the like.

The blade 137 preferably tapers outwardly from the outer surface of the cannula 110 so as to prevent undesirably cutting or damage to the cannula 110 when the blade is moved distally during the cutting process. Such an outward taper or flare of the blade 137 allows some bending of the catheter 110 without the catheter 110 contacting the sharp surface of the blade 137.

Referring now to FIG. 11, the proximal end of either the first or second embodiment of the tissue sampling device of the present invention is shown. According to the preferred embodiment of the present invention a check valve 209 is in fluid communication with the first lumen, at the proximal end thereof, so as to facilitate the proximal flow of fluid through the first lumen 120 and so as to mitigate the distal flow thereof. A Y connection 200 facilitates the introduction of fluid, preferably saline solution, from tube 202 into the second lumen 22, 122. Tube 202 is attaches to a squeeze bulb, syringe, or other fluid supply, as discussed above.

Valved port 204 facilitates the easy extraction of tissue samples from the first lumen 20, 120 by opening the valve or removing the stopper 205 thereof such that the addition of further fluid into the second lumen 22, 122 causes the tissue sample(s) to pass through the lumen 206 of the valve port 204. As discussed above, the first sample collected will be the first sample removed from the first lumen 20, 120.

Figure 5:
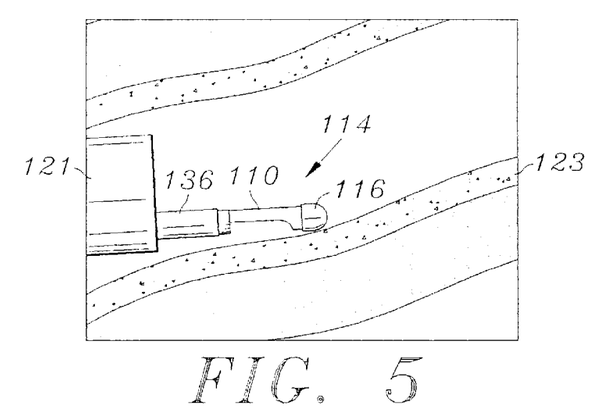
FIG. 5 shows the tissue sampling device of the second embodiment of the present invention being guided into position to remove a desired tissue sample via an endoscope.
Figure 6:
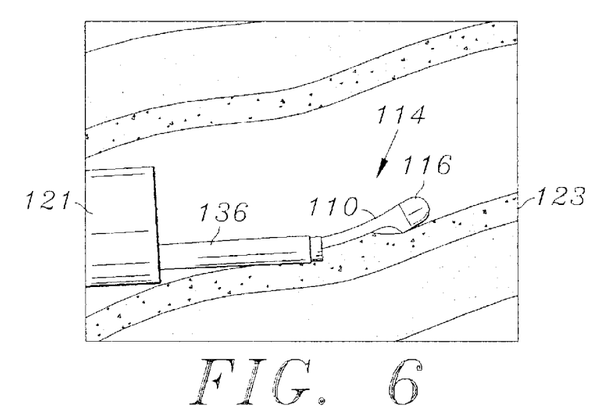
FIG. 6 shows the tissue sampling device of FIG. 5 in the process of collecting a tissue sample, wherein the desired tissue sample is being urged into the opening of the catheter prior to its being cut away from its in-situ anatomical location.
Figure 7:
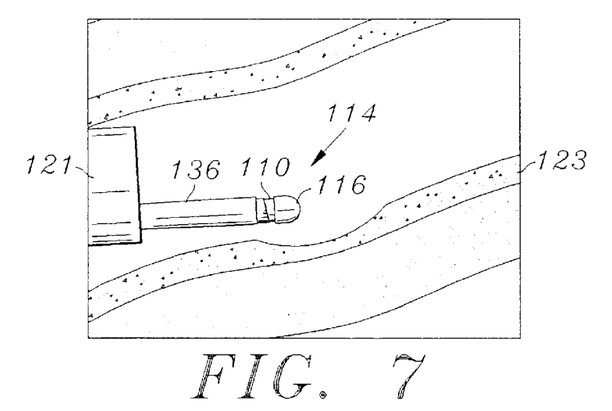
FIG. 7 shows the tissue sampling device of FIG. 6 after the sheath thereof has been moved distally, so as to cut the desired tissue sample away from its in-situ anatomical location.

Referring now to FIGS. 5–7, the use of the tissue sampling device of the second embodiment of the present invention is shown. With particular reference to FIG. 5, the distal end 114 of the catheter 110 is positioned, preferably via an endoscope 121 or the like, at the in-situ anatomical location 123 where the extraction of a tissue sample is desired.

With particular reference to FIG. 6, the distal end 114 of the catheter 110 is urged against the in-situ anatomical location 123 so as to cause a portion of the tissue thereof to enter the first lumen 120 of the catheter 110 through the opening 121 formed therein. This is preferably observed via the endoscope 121.

With particular reference to FIG. 7, once a portion of the tissue at the desired in-situ anatomical location 123 has been urged into the first lumen 120, then the sheath 136 is moved distally while holding the catheter 120 in place, so as to effect cutting and/or tearing of the tissue sample from its in-situ anatomical location 123 and capturing the tissue sample within the first lumen 120 of the catheter 110.

According to either the first or second embodiment of the present invention, after each tissue sample has been captured within the first lumen 20, 120, then fluid is caused to flow through the second lumen 22, 122 of the catheter 10, 110 so as to cause the tissue sample to move proximally. This process may be repeated so as to obtain a plurality of such tissue samples, as desired. Preferably, approximately 0.5 ml of fluid is caused to flow into the second lumen between each sample, so as to provide adequate separation therebetween. Indeed, when the first lumen 20, 120 becomes full, i.e., the first tissue sample reaches the proximal end of the catheter 10, 110, then the tissue samples may be extracted from the catheter 10, 110 through the valve port 204 and the tissue collection procedure continued without requiring extraction of the tissue sampling device from the body, as desired. Preferably, approximately 2 inches to 4 inches of saline solution is provided between each sample, so as to further inhibit cross-contamination. The fluid source may optionally be utilized to flush or clean the cutter between samples, so as to mitigate cross-contamination. In order to perform such flushing, the tissue collector is opened slightly and a small amount of saline is caused to flow therethrough.

The components of both embodiments of the present invention may be formed from biocompatible polymer materials, with the exception of any metal blades, which are preferably formed of stainless steel. As those skilled in the art will appreciate, various biocompatible flexible material such as polyurethane may be utilized where flexibility is required, e.g., for the catheter and/or sheath. The cap for either the first or second embodiment of the present invention may be injection molded and then adhesively or thermally bonded to its respective catheter. All of the components of the first and second embodiments of the present invention may thus be easily and inexpensively fabricated using existing methodology.

The blades of the first and second embodiments of the present invention may be formed by electro-chemically etching the tubular end of a catheter. Only that portion of a catheter which performs cutting of the tissue sample needs to be so sharpened. The blade for the first embodiment of the present invention may optionally comprise a metal blade which is attached to the distal end of the catheter 10, rather than the blade being formed by sharpening the distal end of the catheter 10.

It is understood that the exemplary tissue sampling device described here and shown in the drawings represents only two presently preferred embodiments of the invention. Indeed, various modifications and additions may be made to such embodiments without departing from the spirit and scope of the invention. For example, as those skilled in the art will appreciate, various different types of tissue collectors may be utilized so as to cause tissue sample to be captured within the first lumen of the catheter. Also, as those skilled in the art will appreciate, various different sizes, shapes, and configurations of catheters and/or sheaths are contemplated. Thus, these and other modifications and additions may be obvious to those skilled in the art and may be implemented to adapt the present invention for use in a variety of different applications.

What is claimed is:

1. A tissue sampling device for retrieving multiple tissue samples from a body, the tissue sampling device comprising:
   a) a catheter having proximal and distal ends, the catheter comprising first and second lumens;
   b) a tissue collector formed proximate the distal end of the catheter for removing a tissue sample from its in-situ anatomical location and for capturing the tissue sample within the first lumen of the catheter;
   c) a passage disposed proximate the distal end of the catheter for providing fluid communication between the first and second lumens, the passage being configured such that fluid flowed distally through the second lumen moves the tissue sample proximally through the first lumen; and
   d) wherein moving the tissue sample proximally through the first lumen facilitates collection of a plurality of such tissue samples.

2. The tissue sampling device as recited in claim 1, wherein the first lumen is larger than the second lumen.

3. The tissue sampling device as recited in claim 1, further comprising a deflector for directing fluid from the second lumen to the first lumen, the deflector being configured to direct a substantial portion of the fluid distal of the tissue sample so as to move the tissue sample proximally.

4. The tissue sampling device as recited in claim 3, wherein the deflector comprises an end cap for the catheter, the end cap having a channel formed therein for directing the fluid from the second lumen into the first lumen.

5. The tissue sampling device as recited in claim 1, wherein the deflector comprises a protuberance formed upon an inner wall of the catheter for directing the fluid from the second lumen into the first lumen.

6. The tissue sampling device as recited in claim 1, wherein the tissue collector comprises a seal for mitigating fluid leakage from within the catheter.

7. The tissue sampling device as recited in claim 6, wherein the seal comprises a hermetic seal.

8. The tissue sampling device as recited in claim 1 wherein the tissue collector is configured to cut tissue away from its in-situ anatomical location.

9. The tissue sampling device as recited in claim 1 further comprising a check valve disposed proximate the proximal end of the catheter and in fluid communication with the first lumen so as to facilitate fluid flow proximally therethrough while mitigating fluid flow distally therethrough.

10. The tissue sampling device as recited in claim 1 further comprising:
   a) a check valve disposed proximate the proximal end of the catheter and in fluid communication with the first lumen so as to facilitate fluid flow proximally therethrough while mitigating fluid flow distally therethrough; and b) a valved port in fluid communication with the first lumen through which the tissue samples are withdrawn.

11. The tissue sampling device as recited in claim 1 further comprising a controlled flow fluid source in communication with the first lumen, the controlled flow fluid source selected from the list consisting of:

a) a syringe;

b) a squeeze bulb;

c) a pump;

d) a gravity feed container; and e) a gas pressurize ullage.

12. The tissue sampling device as recited in claim 1 wherein the catheter is configured to pass through a working channel of an endoscope.

13. A tissue sampling device for retrieving multiple tissue samples from a body, the tissue sampling device comprising:

a) a catheter having first and second lumens;

b) a blade formed upon the distal end of the catheter;

c) a cap hingedly attached to the distal end of the catheter proximate the blade, the cap having an open position wherein a tissue sample can be urged into the first lumen of the catheter and having a closed position in which the cap abuts the blade and seals the catheter;

d) an actuator in mechanical communication with the cap for moving the cap from the open position to the closed position thereof;

e) a passage disposed proximate a distal end of the catheter for providing fluid communication between the first and second lumens, the passage being configured such that fluid flowed through the second lumen causes the tissue sample to move proximally through the first lumen; and f) wherein causing the actuator to move the cap from the open position to the closed position thereof causes the blade to cut the tissue sample from its in-situ anatomical location so as to capture the tissue sample within the catheter and wherein moving the tissue sample proximally through the first lumen facilitates collection of a plurality of such tissue samples.

14. The tissue sampling device as recited in claim 13, wherein the blade is formed upon a beveled tip of the catheter.

15. The tissue sampling device as recited in claim 13, wherein the blade comprises a sharpened edge formed upon the distal end of the catheter.

16. The tissue sampling device as recited in Claim 13, wherein the cap is attached to the catheter via a living hinge.

17. The tissue sampling device as recited in claim 13, wherein the actuator comprises a cam formed upon the cap and a sheath within which the catheter is disposed, such that urging the sheath distally with respect to the catheter causes the tube to engage the cam and thus urge the cap into the closed position thereof.

18. The tissue sampling device as recited in claim 13 wherein the cap is configured so as to be biased in the open position thereof.

19. The tissue sampling device as recited in claim 13 wherein the cap is formed from a portion of the catheter wall and is thus curved is a manner which biases the cap in the open position thereof.

20. A tissue sampling device for retrieving multiple tissue samples from a body, the tissue sampling device comprising:

a) a catheter having a proximal end, a distal end, and a lumen;

b) a sheath having a proximal end, a distal end, and a lumen, the catheter being slidably disposed within the lumen of the sheath;

c) a cap closing the distal end of the inner catheter;

d) an opening formed in the catheter proximate the distal end thereof; and e) a blade formed at the distal end of the sheath proximate the cap such that sliding the sheath distally with respect to the inner cannula causes the cap to close and abut the blade, which results in cutting of tissue extending from its in-situ anatomical position through the opening formed in the catheter;

f) a passage disposed proximate the distal end of the catheter for providing fluid communication between the first and second lumens, the passage being configured such that fluid flowed through the lumen causes the tissue sample to move proximally through the first lumen; and g) wherein moving the tissue sample proximally through the first lumen facilitates collection of a plurality of such tissue samples.

21. The tissue sampling device as recited in claim 20, wherein the inner cannula fits within the sheath with a clearance of between approximately 0.001 inch and approximately 0.003 inch.

22. The tissue sampling device as recited in claim 20, wherein the cap comprises a deflector for directing fluid from the second lumen into the first lumen.

23. The tissue sampling device as recited in claim 20, wherein the cap comprises a channel for directing fluid from the second lumen into the first lumen.

24. The tissue sampling device as recited in claim 20 wherein the blade comprises a sharpened portion of the distal end of the sheath.

25. The tissue sampling device as recited in claim 20 wherein the blade comprises a metal blade attached to the distal end of the sheath.

26. A method for collecting multiple tissue samples from a body, the method comprising the steps of:

a) positioning a distal end of a catheter proximate tissue to be sampled;

b) removing a tissue sample from its in-situ anatomical location and capturing the tissue sample within the catheter;

c) flowing a fluid through the catheter so as to cause the tissue sample to move proximally; and d) wherein moving the tissue sample proximally through the catheter facilitates collection of a plurality of such tissue samples.

27. The method as recited in claim 26 wherein the step of capturing the tissue sample within the catheter comprises capturing the tissue sample within a first lumen and the step of flowing a fluid through the catheter comprises flowing the fluid distally through a second lumen and proximally through the first lumen.

28. The method as recited in claim 26 wherein the step of flowing a fluid through the catheter comprises flowing a saline solution through the catheter.

29. The method as recited in claim 26 wherein the step of removing a tissue sample comprises cutting the tissue sample from its in-situ anatomical location.

30. The method as recited in claim 26 wherein the step of removing a tissue sample comprises tearing the tissue sample from its in-situ anatomical location.

31. The method as recited in claim 26 wherein the step of positioning the distal end of the catheter proximate the tissue to be sampled comprises positioning the catheter by guiding it via an endoscope, the catheter being substantially disposed within a working channel of the endoscope.

32. The method as recited in claim 26 wherein the steps of removing a tissue sample from its in-situ anatomical location and capturing the tissue sample within the catheter comprise sequentially removing a plurality of tissue samples from their respective in-situ anatomical locations and capturing each of the tissue samples at spaced apart locations within the catheter.

33. The method as recited in claim 26 wherein the step of flowing a fluid through the catheter comprises generally flowing fluid through the catheter after each tissue sample is captured within the catheter so as to cause the tissue samples to move distally within the catheter.

* * * * *